(12) United States Patent
Smith et al.

(10) Patent No.: US 11,074,656 B2
(45) Date of Patent: Jul. 27, 2021

(54) USING MACHINE LEARNING TO CLASSIFY INSURANCE CARD INFORMATION

(71) Applicant: Walmart Apollo, LLC, Bentonville, AR (US)

(72) Inventors: Walter R. Smith, Seattle, WA (US); Frédéric Médous, San Francisco, CA (US)

(73) Assignee: WALMART APOLLO, LLC, Bentonville, AR (US)

(*) Notice: Subject to any disclaimer, the term of this patent is extended or adjusted under 35 U.S.C. 154(b) by 0 days.

(21) Appl. No.: 16/132,022

(22) Filed: Sep. 14, 2018

(65) Prior Publication Data

US 2019/0080416 A1 Mar. 14, 2019

Related U.S. Application Data

(60) Provisional application No. 62/558,781, filed on Sep. 14, 2017.

(51) Int. Cl.
| | |
|---|---|
| *G06Q 30/00* | (2012.01) |
| *G06Q 40/08* | (2012.01) |
| *G16H 10/60* | (2018.01) |
| *G06N 20/00* | (2019.01) |
| *G16H 40/20* | (2018.01) |
| *G16H 50/70* | (2018.01) |

(52) U.S. Cl.
CPC ............ *G06Q 40/08* (2013.01); *G06N 20/00* (2019.01); *G16H 10/60* (2018.01); *G16H 40/20* (2018.01); *G16H 50/70* (2018.01)

(58) Field of Classification Search
CPC ...................................................... G06Q 40/08
USPC ................ 705/4, 1.1, 35, 44, 51, 3; 370/254
See application file for complete search history.

(56) References Cited

U.S. PATENT DOCUMENTS

| | | | | |
|---|---|---|---|---|
| 8,204,768 B1* | 6/2012 | Grinberg | ............... | G06Q 40/08 705/4 |
| 9,953,372 B1* | 4/2018 | Dziabiak | ............... | G06Q 30/02 |
| 2008/0306761 A1* | 12/2008 | George | ............... | G06Q 10/10 705/2 |

OTHER PUBLICATIONS

ProQuestNPL Search History.*

* cited by examiner

*Primary Examiner* — John H. Holly
(74) *Attorney, Agent, or Firm* — Bryan Cave Leighton Paisner LLP

(57) ABSTRACT

An insurance management system receives, from a client device, at least one image of an insurance card associated with the user operating the client device. The insurance management system extracts features from the at least one image and generates a feature vector associated with the at least one image. A machine learning model receives the feature vector as input and outputs a classification comprising an association with an insurance plan. The insurance management system receives historical medical information that is specific to the user and indicates a current medical condition of the user and evaluates the insurance plan of the user in view of their historical medical information. Based on the evaluation, the insurance management system provides a recommendation that comprises one or more alternative insurance plans or one or more alternative pharmacies.

28 Claims, 9 Drawing Sheets

900

Co-Pay Comparison

ANNUAL SAVINGS     YOUR CURRENT COSTS

$240 /YR   vs.   $55 /MO

Lower prices found near Seattle, WA 98122

| Pharmacy on Main | PLAN PAYS | YOU PAY |
| --- | --- | --- |
| Medication 0.5 mg | $83.25 | $40 |
| Medication 40 mg | $113 | $8 |
| Medication 200 mg | $67.80 | $7 |

| Pharmacy on 11th | | |
| --- | --- | --- |
| Medication 0.5 mg | $92.25 | $30 |
| Medication 40 mg | $121 | $0 |
| Medication 200 mg | $65.80 | $5 |

Change Current Pharmacy 905, 910, 915, 920

FIG. 9

USING MACHINE LEARNING TO CLASSIFY INSURANCE CARD INFORMATION

CROSS-REFERENCE TO RELATED APPLICATION

This application claims the benefit of U.S. Provisional Application No. 62/558,781, filed Sep. 14, 2017, which is incorporated by reference in its entirety.

BACKGROUND

This disclosure relates generally to medical insurance and more specifically to machine learning algorithms applied to insurance cards for identifying and recommending insurance plans.

In today's complex medical insurance market, there are a myriad of choices for medical insurance plans for consumers. The various types of medical insurance plans range from health maintenance organizations (HMOs), preferred provider organizations (PPOs), exclusive provider organizations (EPOs), point-of-service (POS) plans, to high-deductible health plans (HDHPs). Evaluating medical insurance plans as a consumer can be overwhelming when trying to balance the benefits of each plan against the costs of each plan. While insurance policies define intricate cost calculations for healthcare providers and healthcare consumers, they are often written with complicated language and terminology, making the policies challenging to decipher and making it more difficult for consumers to comparison shop. As a result, many consumers enroll in insurance plans that are not the most appropriate for their medical needs and financial budget.

SUMMARY

The present invention involves a method for applying machine-learning algorithms to identify an insurance plan associated with an insurance card of a user and providing a recommendation to the user based on the user's insurance plan. An insurance management system receives, from a client device, at least one image of an insurance card associated with the user operating the client device. The at least one image may include, e.g., a front side of the insurance card and a back side of the insurance card. The insurance management system extracts features from the at least one image, such as text information, object information, color information, and shape information. The insurance management system generates a feature vector associated with the at least one image and inputs the feature vector into a machine learning model that has been trained using classifications of insurance cards of other users. The machine learning model outputs a classification, which comprises an association with an insurance plan. The insurance management system stores the insurance plan of the classification as a current selection of an insurance plan of the user. In one embodiment, the insurance management system receives historical medical information that is specific to the user and indicates a current medical condition of the user. The historical medical information comprises one or more of a prescription history, a medical expense history, a medical claims history, a medical procedure history, and a co-payment history of the user. Based in part on the historical medical information, the insurance management system evaluates the current selection of the insurance plan of the user. Based on the evaluation, the insurance management system provides for display to the user in a user interface a recommendation associated with the current selection of the insurance plan of the user. In one embodiment, the recommendation comprises one or more alternative insurance plans for the user for the user to consider as alternatives to the insurance plan of the user associated with the insurance card. In one embodiment, the historical medical information indicates a pharmacy of the user, and the recommendation comprises one or more alternative pharmacies for the user for the user to consider as alternatives to the pharmacy of the user.

BRIEF DESCRIPTION OF THE DRAWINGS

Figure (FIG. 1 is a block diagram of a system environment in which an insurance management system operates, in accordance with an embodiment.

FIG. 9 is an example of an application feature for comparing medication co-payments, in accordance with an embodiment.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

System Architecture

With dozens of types of health insurance plans, navigating the healthcare insurance landscape can be difficult. Health insurance plans may be offered through government exchanges, private exchanges, an employer, or an insurance provider directly. In addition, several options for types of health insurance plans may be offered (e.g., HMO, PPO, EPO, POS, etc.). Determining the most suitable insurance plan for an individual or a family can be challenging, and often, several individuals and/or families end up choosing the wrong insurance plan.

An insurance management system is configured to manage the insurance information of a user. The system may capture an image of an insurance card of a user via an application on a user's device. The system may scan the image of the insurance card to identify the insurance plan associated with the insurance card. Scanning the image allows the system to extract text, objects, logos, and any other relevant information from the insurance card, which can be input into an insurance data model that classifies the insurance card as being associated with an insurance plan. This thus avoids the extra time of the user having to enter information by hand or deliver details via phone about an insurance plan, and ensures the right information is captured and right plan is identified. The system applies machine learning techniques to the extracted information to improve its classifications of insurance cards and to better identify the insurance plan associated an insurance card. Since there are so many different insurance plans and different insurance card formats, collecting the appropriate information from the card and identifying the correct plan can be challenging. In some embodiments, the insurance management system may be integrated with a prescription management system, which allows the insurance management system to use historical medical information of the user (e.g., prescription history, medical claims history, etc.) to determine if the insurance plan identified from the insurance card information is the most suitable insurance plan for the user. The insurance management system may recommend one or more alternative insurance plans that are more suitable for the user based on the user's medical needs.

Figure 1:
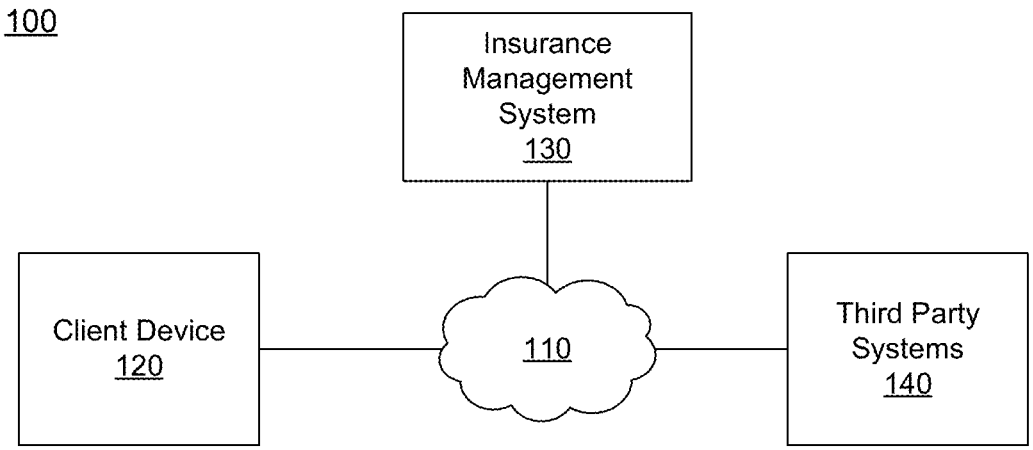

FIG. 1 is a block diagram of a system environment 100 for an insurance management system 130, in accordance with an embodiment. The system environment 100 shown by FIG. 1 comprises a network 110, one or more client devices 120, the insurance management system 130, and one or more third party systems 140. In alternative configurations, different and/or additional components may be included in the system environment 100. The embodiments described herein can be adapted to other suitable online systems that manage insurance information for users.

The client devices 120 are one or more computing devices capable of receiving user input as well as transmitting and/or receiving data via the network 110. In one embodiment, a client device 120 is a conventional computer system, such as a desktop or a laptop computer. Alternatively, a client device 120 may be a device having computer functionality, such as a personal digital assistant (PDA), a mobile telephone, a smartphone or another suitable device. A client device 120 is configured to communicate via the network 110. In one embodiment, a client device 120 executes an application allowing a user of the client device 120 to interact with the insurance management system 130 as a user of an application to access insurance information. For example, the user can use an application that allows the user to use a camera integrated into the client device 120 and allows the user to import images or videos into the application. For example, a client device 120 executes a browser application to enable interaction between the client device 120 and the insurance management system 130 via the network 110. In another embodiment, a client device 120 interacts with the insurance management system 130 through an application programming interface (API) running on a native operating system of the client device 120, such as IOS® or ANDROID™.

The client devices 120 are configured to communicate via the network 110, which may comprise any combination of local area and/or wide area networks, using both wired and/or wireless communication systems. In one embodiment, the network 110 uses standard communications technologies and/or protocols. For example, the network 110 includes communication links using technologies such as Ethernet, 802.11, worldwide interoperability for microwave access (WiMAX), 3G, 4G, code division multiple access (CDMA), digital subscriber line (DSL), etc. Examples of networking protocols used for communicating via the network 110 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 110 may be represented using any suitable format, such as hypertext markup language (HTML) or extensible markup language (XML). In some embodiments, all or some of the communication links of the network 110 may be encrypted using any suitable technique or techniques.

The insurance management system 130 manages the insurance information of a user. The user may interact with the insurance management system 130 through an application on the client device 120 of the user. In some embodiments, the insurance information may be entered by a user into the application, or the insurance information may be extracted from an image of the insurance card of the user that is imported into or taken through the application on the client device 120. The insurance information may include one or more of the following: a patient name, an insurance carrier name, an insurance plan name, a patient identification number, an issuer identification number, a group number, a coverage effective date, an employer name, a bank identification number (BIN), co-payment information, a customer service number, and any other relevant insurance information. The insurance information may be located on a front side or a back side of the insurance card.

The insurance management system 130 may analyze the insurance information of the user. Using the information extracted from the insurance card, the insurance management system 130 may use machine learning techniques to classify the insurance card as being associated with a type of insurance plan provided to the user. The insurance management system 130 may store the classifications of insurance cards from several users to build a database of existing insurance plans. Applying machine learning techniques allows the insurance management system 130 to improve its classifications of insurance cards and to better identify the insurance plan associated with an insurance card. In some embodiments, the insurance management system 130 may be integrated with a prescription management system, as described in U.S. patent application Ser. No. 14/656,691 filed on Mar. 12, 2015, which is fully incorporated herein by reference. In these embodiments, the insurance management system 130 uses historical medical information of the user (e.g., prescription history, medical claims history, etc.) to determine if the insurance plan identified from the insurance card information is the most suitable insurance plan for the user. The insurance management system 130 may recommend one or more alternative insurance plans that are more suitable for the user based on the user's medical needs. While described as separate systems, the insurance management system 130 and the prescription management system may be part of a larger system in some embodiments.

One or more third party systems 140 may be coupled to the network 110 for communicating with the insurance management system 130, which is further described below in conjunction with FIG. 2. In one embodiment, a third party system 140 is an application provider communicating information in databases or keys for accessing information in databases by a client device 120. A third party system 140 may also communicate information in databases or keys for accessing information in databases to the insurance management system 130. These databases may include information from a prescription management system, a publicly available database of insurance plans (e.g., Medicare), or personal accounts of the user to which access by the insurance management system 130 has been authorized.

Figure 2:
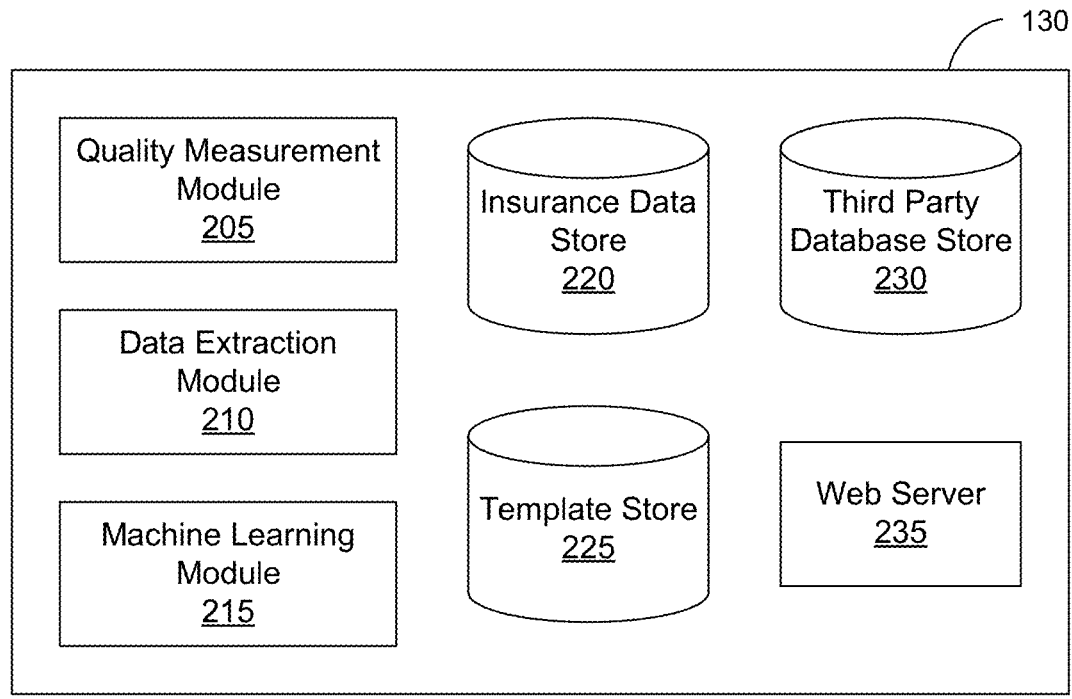
FIG. 2 is a block diagram of an insurance data management system, in accordance with an embodiment.

FIG. 2 is a block diagram of an architecture of the insurance management system 130, in accordance with an embodiment. The insurance management system 130 shown in FIG. 2 includes a quality measurement module 205, a data extraction module 210, a machine learning module 215, an insurance data store 220, a template store 225, a third-party database store 230, and a web server 235. In other embodiments, the insurance management system 130 may include additional, fewer, or different components for various applications. Conventional components such as network interfaces, security functions, load balancers, failover servers, management and network operations consoles, and the like are not shown so as to not obscure the details of the system architecture. For example, as previously described, the insurance management system 130 may use historical medical information from other systems, such as a prescription management system. The information may include prescription information, medical claims history, or any other relevant medical information.

The quality measurement module 205 determines one or more quality measurements of an image where a quality measurement is associated with one or more adjustments in an image. An adjustment of an image can be a filter applied to an image or an adjustment of orientation, brightness, contrast, hue, saturation, color balance, one or more color vibrancies, levels, curves, exposure, thresholds, luminance, and any other suitable adjustment that can be made to an image. The quality measurement module 205 determines one or more quality measurements of an image and, based on the quality measurements, provides information describing the quality measurements to a user of the system 130. The provided information can include suggestions, instructions, or guidelines for improving quality of the images based on the quality measurements, as described further below in conjunction with FIGS. 3, 4A, and 4B.

The data extraction module 210 identifies or extracts machine-readable information or text in an image using one or more text recognition algorithms, one or more object recognition algorithms, or any other suitable feature recognition algorithm. The data extraction module 210 accesses images of an insurance card where each image includes a partial or full view of a front side or a back side of the insurance card. Associations are determined between the identified text and one or more types of information where a type of information can be information about an insurance plan or information about the user. In one embodiment, the data extraction module 210 determines these associations based on a determination of a template that matches (or matches with a threshold level of confidence) the insurance card. A template is a geometrical representation of an insurance card known to the insurance management system 130. For example, if the template is known to have a certain type of information in a first slot in an upper right corner of an insurance card, then the identified text in the upper right corner of the insurance card is associated with the certain type of information. The identified text in an insurance card and determined associations of the identified text with one or more types of information is stored in the insurance data store 220. The function provided by the data extraction module 210 is further described below in conjunction with FIG. 6.

The machine learning module 215 applies machine learning techniques to generate an insurance data model that when applied to images of insurance cards outputs a classification associated with the information on the insurance card. In the embodiment of FIG. 2, the classification indicates a probability that the insurance card is associated with a specific type of insurance plan. In other embodiments, the classification may indicate a confidence level that the insurance card matches a template, a probability that the insurance card is associated with a specific insurance company, or some combination thereof.

As part of the generation of the insurance data model, the machine learning module 215 forms a training set of images of insurance cards by identifying a positive training set of images of insurance cards that have been accurately classified as being associated with a specific type of insurance plan. In some embodiments, the machine learning module 215 forms a negative training set of images of insurance cards as not belonging to a specific insurance company or being associated with a specific type of insurance plan. The training set of images may be reviewed manually by reviewers or automatically by the system 130.

The machine learning module 215 extracts feature values from the images of insurance cards of the training set, the features being variables deemed potentially relevant to classifying the insurance cards. Specifically, the feature values extracted by the machine learning module 215 include text, font size and/or style, logos or objects, color, shape, or any other relevant feature that may be extracted from an image. An ordered list of the features for an insurance card is herein referred to as the feature vector for the insurance card. In one embodiment, the machine learning module 215 applies dimensionality reduction (e.g., via linear discriminant analysis (LDA), principle component analysis (PCA), or the like) to reduce the amount of data in the feature vectors for insurance cards to a smaller, more representative set of data.

The machine learning module 215 uses supervised machine learning to train the insurance data model, with the feature vectors of the positive training set and the negative training set serving as the inputs. Different machine learning techniques—such as linear support vector machine (linear SVM), boosting for other algorithms (e.g., AdaBoost), neural networks, logistic regression, naïve Bayes, memory-based learning, random forests, bagged trees, decision trees, boosted trees, or boosted stumps—may be used in different embodiments. The insurance data model, when applied to the feature vector extracted from an insurance card, outputs a classification of the insurance card as being associated with a type of insurance plan, such as a Boolean yes/no estimate or a scalar value representing a probability.

In some embodiments, a validation set is formed of additional images of insurance cards, other than those in the training sets, which have already been classified as being associated or not associated with a type of insurance plan. The machine learning module 215 applies the trained validation insurance data model to the images of insurance cards of the validation set to quantify the accuracy of the insurance data model. Common metrics applied in accuracy measurement include: Precision=TP/(TP+FP) and Recall=TP/(TP+FN), where precision is how many the insurance data model correctly classified (TP or true positives) out of the total it classified (TP+FP or false positives), and recall is how many the insurance data model correctly classified (TP) out of the total number of insurance cards that were classified (TP+FN or false negatives). The F score (F-score=2*PR/(P+R)) unifies precision and recall into a single measure. In one embodiment, the machine learning module 215 iteratively re-trains the insurance data model until the occurrence of a stopping condition, such as the accuracy measurement indication that the model is sufficiently accurate, or a number of training rounds having taken place.

The insurance data store 220 stores insurance information of users of the insurance management system 130. In one embodiment, the stored insurance information is stored in association with identifiers of users and, in another embodiment, the insurance data store 220 stores one or more user profiles associated with users of the insurance management system 130 and each user profile associated with a user includes insurance information associated with the user. The insurance data store 220 may also store the one or more images of the insurance card associated with the insurance information of the user and may store the classifications associated with the one or more images of the insurance card of the user.

The template store 225 stores one or more templates and the companies and/or insurance plans associated with the one or more templates. A template is a geometrical representation of an insurance card known to the insurance management system 130. For example, if insurance company A is known to use a first type of insurance card for a first insurance plan and a second type of insurance card for a second insurance plan, the template store 225 stores a first template for the first insurance plan, a second template for the second insurance plan, and an association with insurance company A with the first and second types of templates. Thus, if Anthem® is known to use a certain template for an insurance card for a family insurance plan, then the template store 225 can store the template in association with Anthem® and the type of insurance plan. Each template in the template store 225 includes one or more slots and, for each slot in the template, stores a type of information associated with the slot. For example, if a first slot in a template is known to be associated with a first type of information (e.g., user name), then the template store 225 stores the first slot in the template in association with the first type of information. In one embodiment, a location of the first slot in the template is associated with the first type of information.

The third-party database store 230 stores information from one or more databases associated with third party systems 140 or keys accessing information in one or more databases associated with third party systems 140. For example, if a known insurance company is company A, then the insurance management system 130 may have access to company A's databases and company A may have access to the insurance data store 220 of the insurance management system 130. In one embodiment, information associated with a user of the system 130 included in a database in a third party system 130 is only accessible by the system 130 if the user gives permission for the information to be transferred.

The web server 235 links the insurance management system 130 via the network 110 to the one or more client devices 120, as well as to the one or more third party systems 140. The web server 235 serves web pages, as well as other content, such as JAVA®, FLASH®, XML, and so forth. The web server 235 may receive and route messages between the insurance management system 130 and the client device 120, for example, information describing quality measurements, insurance cards, or other suitable messages. Additionally, the web server 235 may provide application programming interface (API) functionality to send data directly to native client device operating systems, such as IOS®, ANDROID™, WEBOS® or BlackberryOS.

Preprocessing an Image Using Quality Measurements

Figure 3:
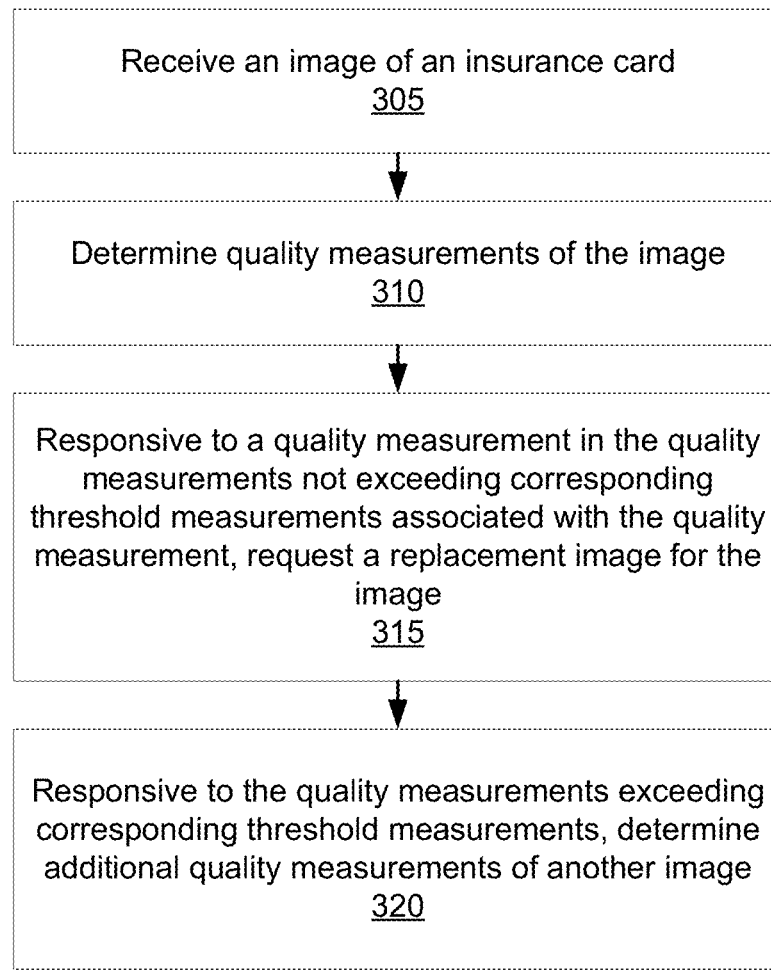
FIG. 3 is a flowchart of a method for preprocessing an image using quality measurements, in accordance with an embodiment.

FIG. 3 is a flowchart of a method for preprocessing an image using quality measurements, in accordance with an embodiment. In various embodiments, the steps described in conjunction with FIG. 3 may be performed in different orders. Additionally, in some embodiments, the method may include different and/or additional steps than those shown in FIG. 3. The functionality described in conjunction with the insurance management system 130 in FIG. 3 may be provided by the quality measurement module 205, in one embodiment, or may be provided by any other suitable component, or components, in other embodiments. Additionally, the client device 120 may execute one or more instructions associated with the insurance management system 130, such as an application associated with the insurance management system 130, to provide the functionality described in conjunction with FIG. 3.

The system 130 receives 305 an image of an insurance card associated with a user from a client device operated by the user. Each image is of a front side or a back side of the insurance card. The insurance card may include insurance information regarding one or more of the following: a patient name, an insurance carrier name, an insurance plan name, a patient identification number, an issuer identification number, a group number, a coverage effective date, an employer name, a bank identification number (BIN), co-payment information, a customer service number, and any other relevant insurance information. The insurance information may be located on a front side or a back side of the insurance card. In some embodiments, the system 130 receives 305 a first image of a first side of the insurance card and then receives 305 a second image of a second side of the insurance card. In some embodiments, the front image and the back image may be combined as a single image by the system 130.

In alternative embodiments, the images can be a video feed and can be automatically captured by an application executing on the client device operated by the user that is associated with the system 130. For example, a video feed or images can be captured automatically based on camera motion (based on motion data from a motion sensor integrated in the client device 120), values associated with pixels in the image, any suitable real-time analysis of the images, information describing an environment where the image or video feed is being captured, or any combination thereof. In these embodiments, the system 130 may be configured to detect objects that are shaped similar to a card (e.g., square, rectangular, etc.). The system 130 may detect the corners and/or the edges of the object and apply a transformation (e.g., reverse perspective, homography, etc.) on the object to capture an image of a certain quality. For example, the system 130 may determine the four edges of the card in the image and apply a homography to normalize the card to a substantially flat rectangle (i.e., transforming a card that is diagonal or at an angle, such as illustrated in FIG. 4B, to a rectangle having a standard card aspect/ratio). In this configuration, the system 130 captures an image of, e.g., a flat rectangular card even if a camera of the client device is not oriented head-on or parallel to the card. The image can be captured automatically once a frame of the video feed has a quality measurement above a certain threshold.

One or more quality measurements of the image are determined 310. Each quality measurement is associated with one or more adjustments in the image. An adjustment of an image includes adjusting brightness, contrast, hue, saturation, color balance, one or more color vibrancies, levels, curves, exposure, thresholds, luminance, and any other suitable adjustment that can be made to an image. The adjustment of an image can also be a filter applied to the image. A quality measurement of an image is a measurement of an adjustment of the image. For example, if the adjustment of the image is contrast, then the quality measurement of the image can be a measurement of how much contrast has been adjusted for the image. Responsive to determining 310 one or more quality measurements of the image, the system 130 can present information to the user describing the quality measurements, as further described below in conjunction with FIGS. 4A and 4B. Similarly, the system 130 can present to the user, via an application executing on a client device 120 operated by the user, instructions for rotating the insurance card in a certain orientation, as further described below in conjunction with FIGS. 4A and 4B.

In response to a quality measurement (e.g., in the one or more quality measurements determined as described above) not exceeding one or more threshold measurements associated with one or more adjustments of the quality measurement, the system 130 requests 315 a replacement image for the image. In one embodiment, the one or more quality measurements are for lighting, camera motion, and focus. Thus, an application associated with the system 130 executing on the client device 120 checks for lighting, camera motion, and focus through luminance values in an image, motion data associated with the client device 120, and edge density analysis, respectively.

The application can check for sufficient lighting through the luminance values of the image. The application extracts the luminance values of the image and, if the captured image is in YUV format, the luminance values are simply the Y components of the pixel values. If the image is in another format, a color space transform can be applied to the image to convert the image into YUV format. The application or the server 130 can determine a histogram of the luminance values and determine brightness and a contrast of the image based on a minimum value associated with the histogram, a maximum value associated with the histogram, a difference between the minimum value and the maximum value, or any combination thereof. Responsive to brightness, contrast, or both brightness and contrast of the image not exceeding corresponding threshold measurements associated with brightness, contrast, or both brightness and contrast, respectively, the application can display information to the user describing the brightness and contrast of the image. For example, the information displayed can include a message encouraging the user to increase the ambient lighting, a message informing the user that more light is needed for accuracy, or any other suitable message assisting the user in capturing an image with better quality.

The application can check for camera motion via an accelerometer or any other suitable motion sensor integrated into the client device 120 operated by the user executing the application. For an accelerometer, if a magnitude of the accelerometer readings is above a threshold measurement associated with the accelerometer readings, the application can display information to the user describing the motion of the camera and whether the camera needs to be steadier during image capture.

The application or the system 130 can also check for focus by applying one or more filters to an image. For example, the application can apply a Gaussian blur filter to the image to eliminate spurious high-frequency artifacts, a Laplacian filter to detect edges, or any combination thereof. An edge density value associated with the image after the image is filtered can be determined. The edge density value can be an average edge density value for a plurality of sample points in the image, a maximum edge density value associated with the image, or any other suitable combination of edge density values in the image. If the edge density value does not exceed a threshold measurement associated with edge densities, the application can display information to the user describing edge density in the image. The threshold measurement for edge densities can be based on empirical testing on various device models and configurations.

The system 130 can determine one or more threshold measurements corresponding to one or more quality measurements measuring adjustment levels of an image. Thus, a quality measurement of an image exceeding a corresponding threshold measurement represents the image having an adjustment of the image that does not lessen the quality of the image. For example, if the quality measurement of an image is a measurement of contrast, then the quality measurement exceeding a corresponding threshold measurement associated with contrast represents the image having enough contrast that details in the image are recognizable, such as text in the image. In another embodiment, a quality measurement of an image not exceeding a corresponding threshold measurement represents the image having an adjustment of the image that does not lessen the quality of the image. For example, if the quality measurement of an image is a measurement of exposure, then the quality measurement not exceeding a corresponding threshold measurement associated with exposure represents the image not having too much exposure so that details in the image such as text are recognizable. Rather than or in addition to threshold measurements, the system 130 can determine ranges of measurements associated with adjustment levels of an image. Thus, a quality measurement of an image that is within the range of measurements represents the image having an adjustment of the image that is within a range that does not lessen the quality of the image. The system 130 can also present information to the user describing whether one or more of the quality measurements exceed corresponding threshold measurements, do not exceed corresponding threshold measurements, are within a range of measurements determined by the system 130, or any combination thereof, as further described below in conjunction with FIGS. 4A and 4B.

In response to the one or more quality measurements exceeding corresponding threshold measurements associated with adjustments for the quality measurements, the system 130 determines 320 one or more additional quality measurements of another image (e.g., of the second side of the insurance card). If each of the quality measurements exceed corresponding threshold measurements, do not exceed corresponding threshold measurements, are within a range of measurements determined by the system 130, or any combination thereof, then the quality of the image is suitable for identifying details and features in the image. The system 130 can also determine whether the images capture the front side and the back side of the insurance card. Where each image has quality measurements exceeding corresponding threshold measurements, the images can be stored in the insurance data store 220.

User Interface

Figure 4A:
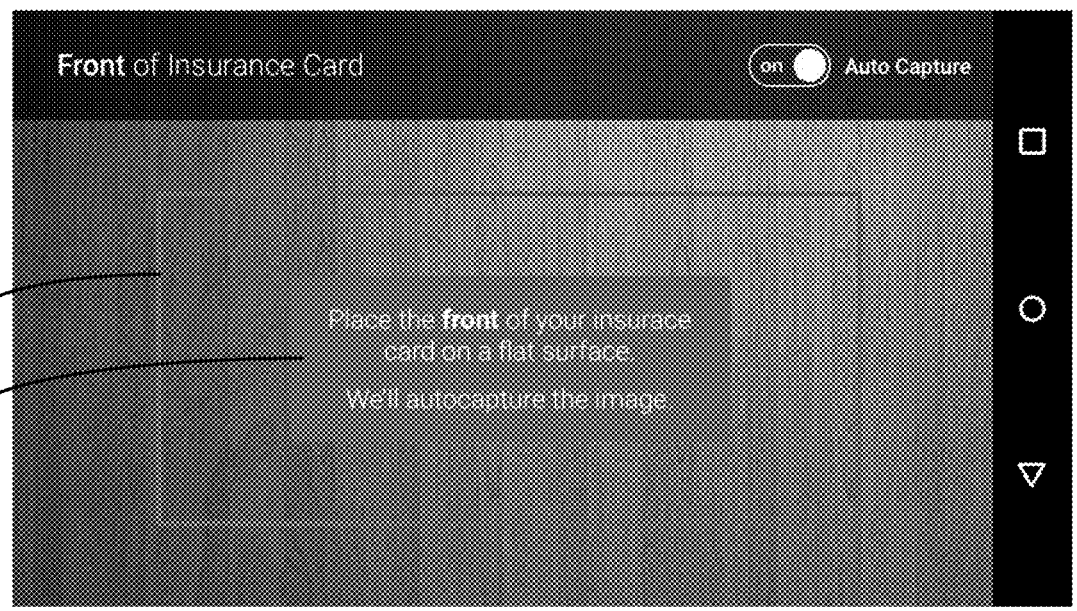
FIGS. 4A, 4B, 4C, and 4D illustrate a user interface for capturing an image of an insurance card, in accordance with an embodiment.
Figure 4B:
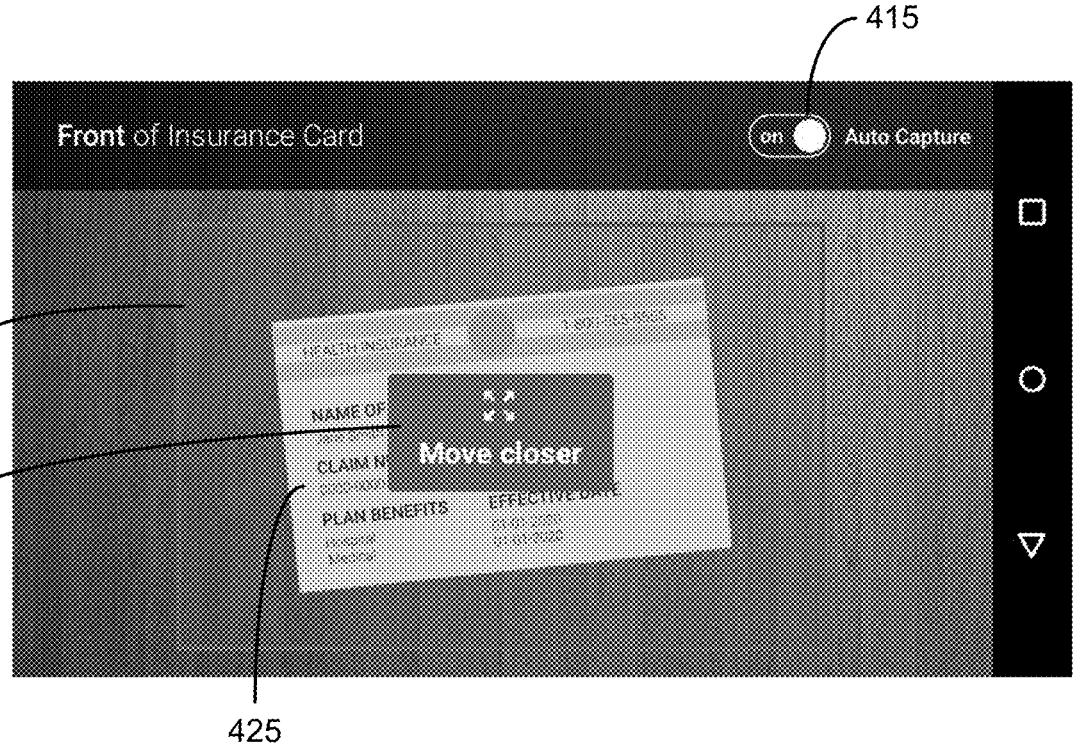

FIGS. 4A, 4B, 4C, and 4D illustrate a user interface 400 for capturing an image of an insurance card, in accordance with an embodiment. The system 130 may display the user interface 400 to the user during initialization of the application, or the user may skip this step during initialization and may later initiate the user interface 400 through the settings of the application. If skipped, the system 130 may send a reminder to the user to complete this insurance card step. As shown in FIG. 4A, the system 130 can provide guidelines 405 to a client device 120 operated by a user for presentation to the user in the user interface 400 on an application executing on the client device 120. In addition to the guidelines 405, the system 130 can also present instructions 410 to the user. For example, FIG. 4A presents "Place the front of your insurance card on a flat surface. We'll autocapture the image." The application may automatically capture images responsive to detecting the insurance card aligned within the guidelines 405. As shown in FIG. 4A, the user interface includes a toggle button 415 to turn on and off the autocapture. Additional examples of instructions include "Place the back of your insurance card on a flat surface," "frame and focus the insurance card," and "capture all of the insurance card," which can also be presented to the user via a client device 120 operated by the user prior to capturing images.

As shown in FIG. 4B, the system 130 can also present information 420 in the user interface 400 describing quality measurements associated with a captured image or a real-time video feed. The information can describe whether a quality measurement of an adjustment in a captured image or real-time video feed is above or below a threshold measurement associated with the adjustment. Thus, if the lighting is poor based on luminance values in an image not exceeding threshold luminance values, the information 420 can state "LOW LIGHT—Please use better lighting." If the focus is poor based on motion data of the client device 120 or edge density values associated with an image exceeding threshold measurements associated with motion data or threshold measurements associated with edge density values, respectively, the information 420 can state "OUT OF FOCUS—Please move the card farther away from the camera." As shown in FIG. 4B, an insurance card 425 does not adequately fill the guidelines 405; thus, the information 420 states "Move closer" and depicts arrows to instruct the user to fill the guidelines 405 with the insurance card 425.

Figure 4C:
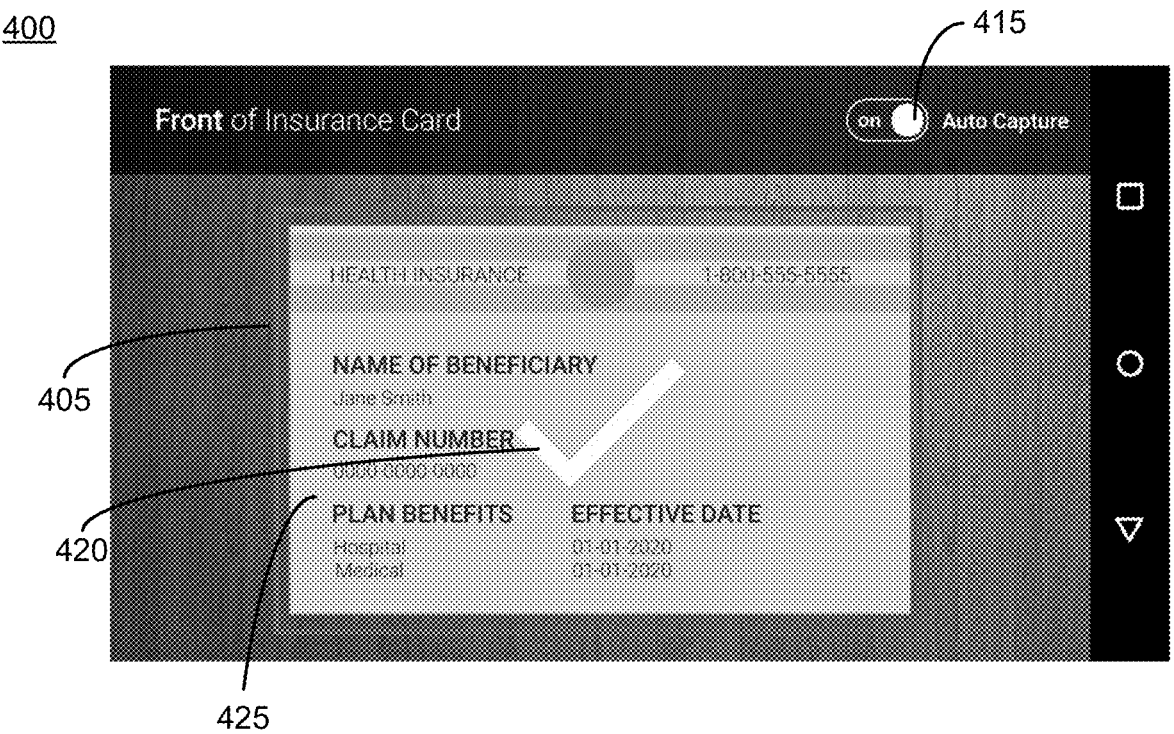

As shown in FIG. 4C, the system 130 presents information 420 in the user interface 400 that indicates an image of the insurance card 425 is captured. In the embodiment of FIG. 4C, the autocapture toggle button 415 is in the "ON" position. In an autocapture mode, the system 130 may capture an image of the insurance card 425 responsive to detecting that all quality measurements are above or below a respective threshold measurement. FIG. 4C illustrates that the insurance card 425 adequately fills the guidelines 405, and the lighting, contrast, and focus of the insurance card 425 are sufficient such that the text on the insurance card 425 is legible. If the autocapture mode is off, a user may provide a user input via the user interface 400 to capture an image of the insurance card 425. In some embodiments, the information 420 presented in FIG. 4C may indicate that the insurance card 425 is appropriately positioned within the guidelines 405 and is ready to be captured.

Figure 4D:
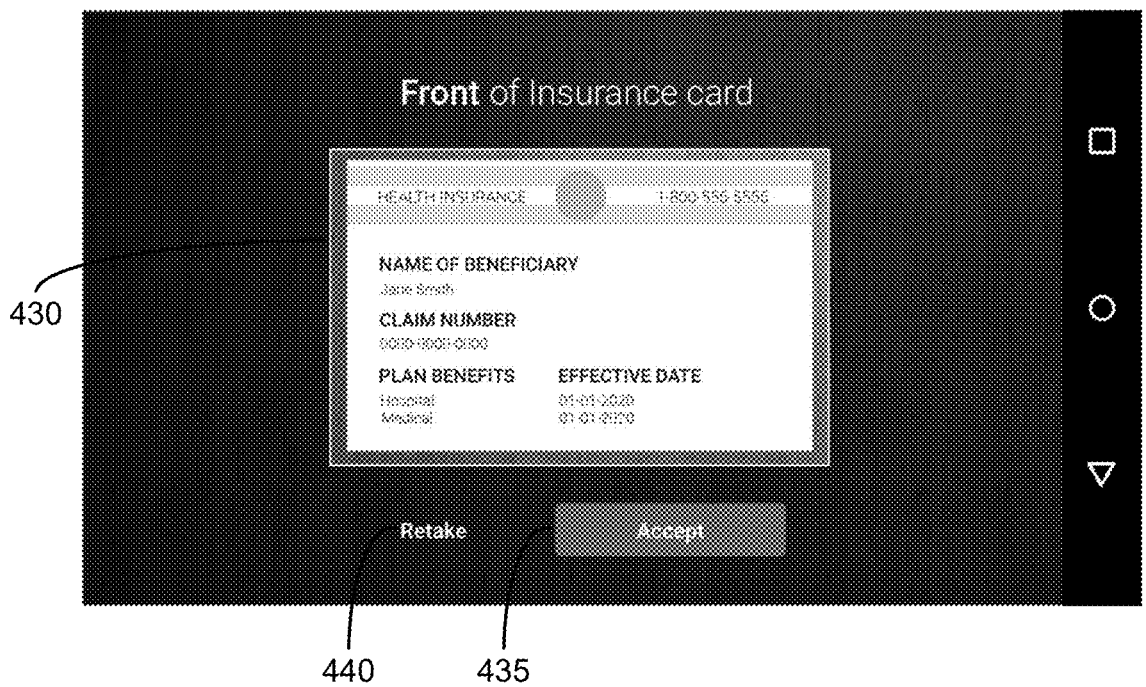

As shown in FIG. 4D, the system 130 presents a captured image 430 of the insurance card 425 in the user interface 400. The user interface 400 allows a user to review the captured image 430 to ensure that the quality of the captured image 430 is sufficient. The user interface 400 offers the user an "Accept" option 435 if the captured image 430 is acceptable and can be stored in association with the user and a "Retake" option 440 if the captured image 430 should be retaken. If a user chooses the "Accept" option 435, the system 130 may store the captured image 430 in association with the user. If a user chooses the "Retake" option 440, the system 130 may delete the captured image 430 and return the user to the user interface shown in FIG. 4A or FIG. 4B.

Using Information from the Image of the Insurance Card

Figure 5:
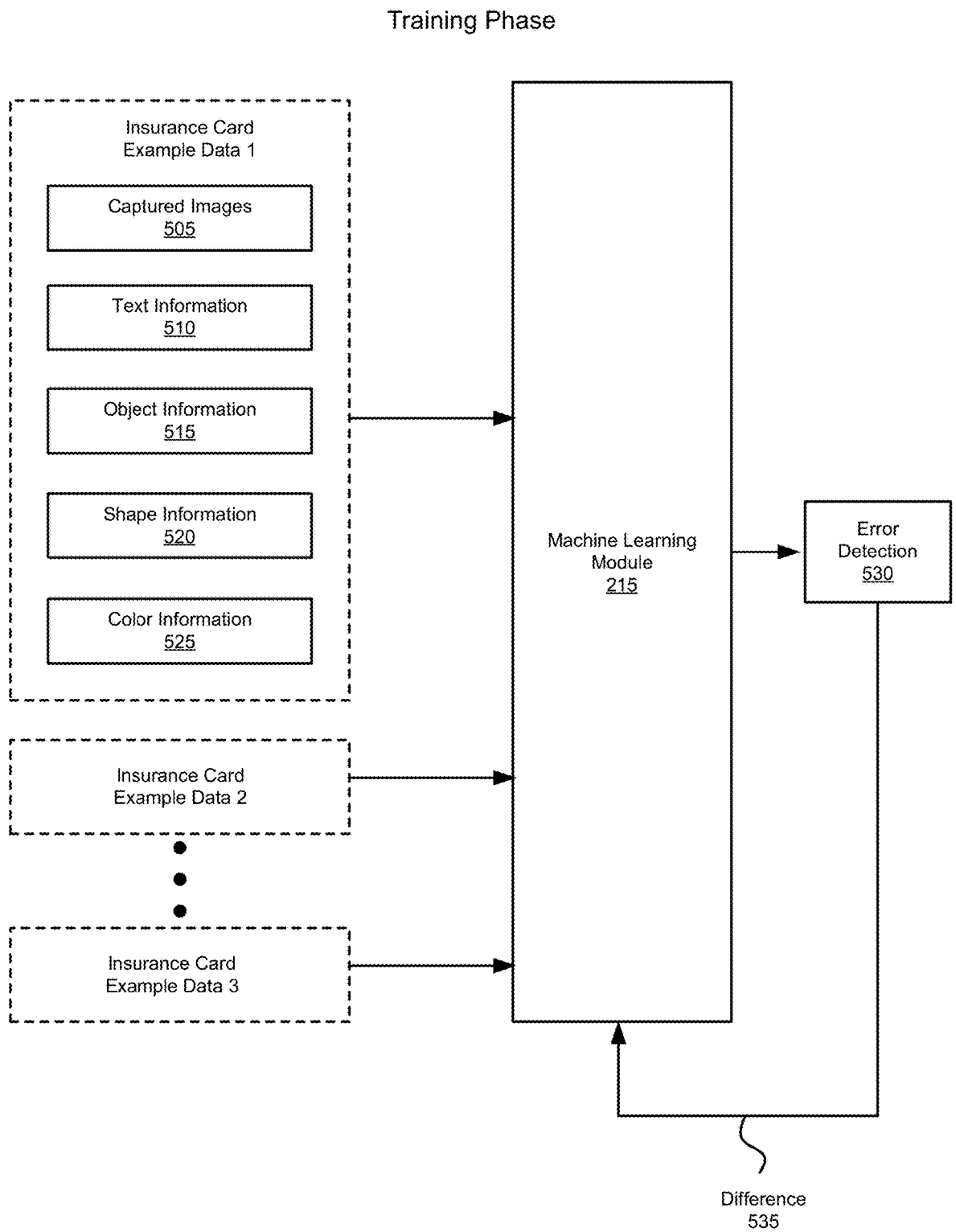
FIG. 5 is a schematic block diagram of a training phase of a machine learning module, in accordance with an embodiment.

FIG. 5 is a schematic block diagram of a training phase of the machine learning module 215, in accordance with an embodiment. During the training phase, the machine learning module 215 implements a learning algorithm to learn how to classify an insurance card as being associated with an insurance plan. The machine learning module 215 inputs into its model a large number of examples of insurance cards of a training set. As described with regards to FIG. 2, the training set may be a positive training set or a negative training set, where the example insurance cards are classified as associated or not associated, respectively, with an insurance plan. The machine learning module 215 learns using these examples to determine a set of coefficients for the insurance data model, enabling the insurance data model to output classifications of other insurance cards as being associated with an insurance plan. In some embodiments, the machine learning module 215 identifies or creates one or more templates based on the learned examples and stores the templates in the template data store 225 such that the templates may be later used to determine a match between other insurance cards and the templates.

In the embodiment of FIG. 5, the machine learning module 215 inputs data from several examples of insurance cards that have been previously classified as associated or not associated with an insurance plan. As illustrated in FIG. 5, an example includes a set of features comprising one or more captured images 505, text information 510, object information 515, shape information 520, and color information 525. The text information 510, object information 515, shape information 520, and color information 525 may be information extracted from the one or more captured images 505. In alternate embodiments, the set of features for an example may include different types of combinations of information. For example, the examples may be associated with a template such that the machine learning module 215 may also learn how to determine a match between the example insurance card and the template. The captured images 505 may include multiple images of the insurance card, e.g., an image of the front side and an image of the back side. The text information 510 includes text on the insurance card that may be identified using text recognition algorithms, where the text includes one or more of the following: a patient name, an insurance carrier name, an insurance plan name, a patient identification number, an issuer identification number, a group number, a coverage effective date, an employer name, a bank identification number (BIN), co-payment information, and a customer service number. The object information 515 may include one or more logos, images, or some combination thereof on the insurance card. The shape information 520 includes a shape of the insurance card, e.g., rectangular or square. The color information 525 may include color of text on the insurance card, a background color of the insurance card, color of one or more logos or images, or some combination thereof.

The machine learning module 215 receives as input, for each example insurance card, the captured images 505, the text information 510, the object information 515, the shape information 520, and the color information 525, and then, for each example, outputs a classification of an insurance plan associated with the example insurance card. The machine learning module 215 performs error detection 530 and compares the output classification to the actual classification of the insurance card. Based on a calculated difference 535, the machine learning module 215 may adjust the coefficients of its insurance data model to reduce the detected error. The machine learning module 215 may perform the training process multiple times for one or more example insurance cards that it receives.

In some embodiments, the machine learning module 215 trains the insurance data model using the positive training set or the negative training set and then validates the insurance data model using the validation training set. In these embodiments, the machine learning module 215 determines the coefficients of the insurance data model using the positive training set or the negative training set and then inputs the example insurance cards of the validation training set to the insurance data model to perform error detection 530. The machine learning module compares the output classifications to the actual classifications of the example insurance cards of the validation training set. Performing error detection 530 may include evaluating the insurance data model using one or more of the metrics described with regard to FIG. 2, e.g., precision, recall, the F score, or some combination thereof. The machine learning module 215 may iteratively train the insurance data model until the occurrence of a stopping condition, such as the difference 535 is below a specified threshold, the accuracy measurement indication that the model is sufficiently accurate, or a number of training rounds having taken place.

Figure 6:
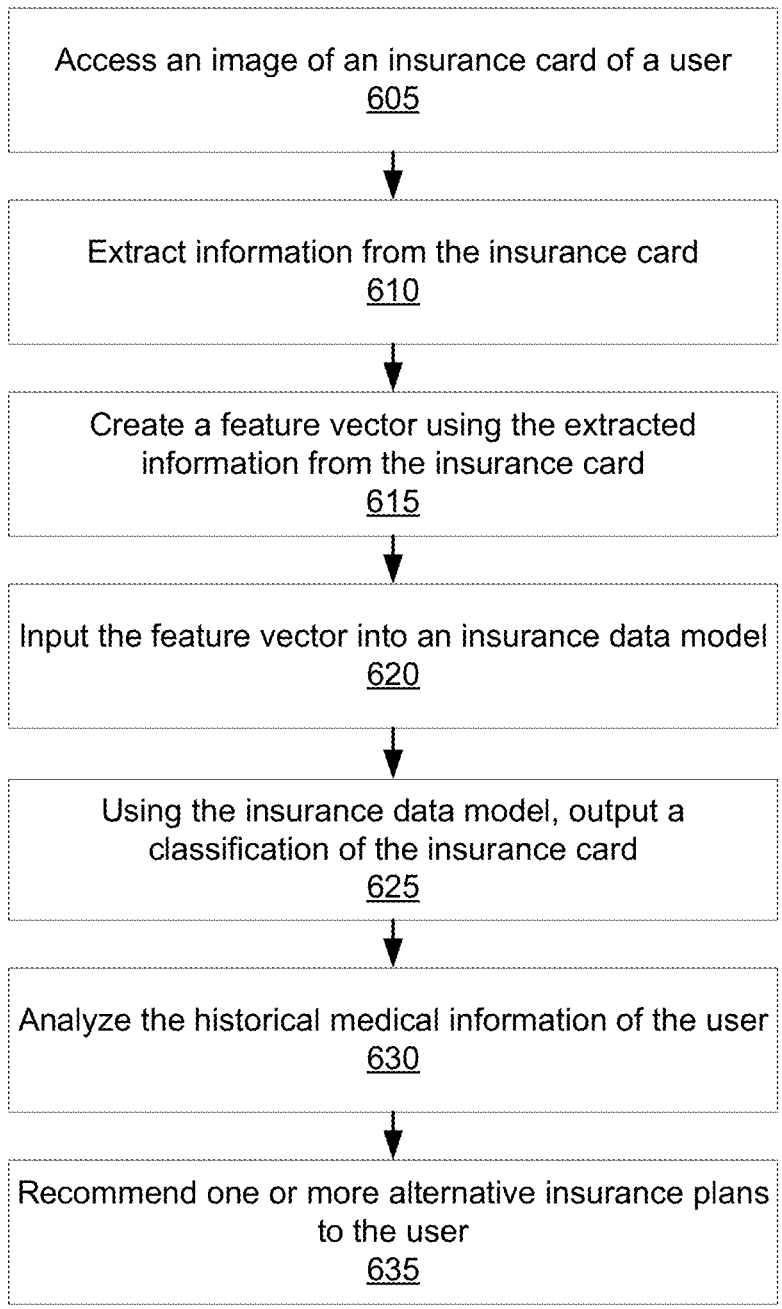
FIG. 6 is a flowchart of a method for applying machine learning techniques to an image of an insurance card, in accordance with an embodiment.

FIG. 6 is a flowchart of a method 600 for applying machine learning techniques to an image of an insurance card, in accordance with an embodiment. In various embodiments, the steps described in conjunction with FIG. 6 may be performed in different orders. Additionally, in some embodiments, the method may include different and/or additional steps than those shown in FIG. 6. The functionality described in conjunction with the insurance management system 130 in FIG. 6 may be provided by the quality measurement module 205, the data extraction module 210, and the machine learning module 215, or may be provided by any other suitable component, or components, in other embodiments. Additionally, the client device 120 may execute one or more instructions associated with the insurance management system 130, such as an application associated with the insurance management system 130, to provide the functionality described in conjunction with FIG. 6.

The system 130 accesses 605 an image of an insurance card of a user. Each image is associated with a front side or a back side of the insurance card. In some embodiments, the system 130 accesses 605 multiple images of the insurance card, e.g., an image of the front side and an image of the back side. The accessed image(s) may be the image(s) received 305 from the method described in conjunction with FIG. 3. As previously described in conjunction with FIG. 3, one or more quality measurements associated with each image can be determined 310 and compared to threshold measurements to determine whether a new image is needed.

The system 130 extracts 610 information from the insurance card. The extracted information may include text, font size and/or style, logos or objects, color, shape, or any other relevant feature that may be extracted from an image. In addition, the system 130 can extract 610 other features on the insurance card such as a barcode, a QR code, or any other suitable machine-readable representation of data. Text on the insurance card may be identified using text recognition algorithms. For example, the system 130 may use optical character recognition, optical word recognition, intelligent character recognition, intelligent word recognition, or any other suitable text recognition algorithm. Based on patterns of characters in the extracted text, the system 130 can associate various patterns of the characters in the extracted text with types of information. For example, if the characters include five numbers, then the system 130 can associate the five numbers with a zip code. If the characters include ten numbers, the system 130 can associate the ten numbers as a phone number.

The system 130 creates 615 a feature vector using the extracted information from the insurance card. The feature vector is an ordered list of the features for the insurance card. In one embodiment, the system 130 applies dimensionality reduction (e.g., via linear discriminant analysis (LDA), principle component analysis (PCA), or the like) to reduce the amount of data in the feature vectors for insurance cards to a smaller, more representative set of data.

The system 130 inputs 620 the feature vector into an insurance data model. The system 130 uses the insurance data model to determine if the insurance card associated with the feature vector is associated with a type of insurance plan. In some embodiments, the insurance data model allows the system 130 to determine if the insurance card matches a template. As previously described, each template is associated with one or more slots of the template associated with a type of information. For example, a template associated with a company and, based on the association with the company, various slots in the template are associated with a type of information provided on the insurance card. For example, a template can include a slot that is a designated sub portion of the insurance card for a type of information such as information about an insurance plan or information about the user. If the feature vector associated with the insurance card includes a name of a company, then the system 130 may determine that the insurance card may use a template that the company is known to use. As an example, if Aetna® is known to use a certain type of template and the feature vector includes text having the sequence of characters "Aetna," then the system 130 determines that the insurance card may use the certain type of template. In some instances, the system 130 may determine that the template used by the company is not the template of the insurance card based on the feature vector associated with the insurance card.

The system 130 outputs 625 a classification of the insurance card using the insurance data model, which allows the system 130 to identify the insurance plan on the insurance card. The classification indicates if the insurance card is associated with a specific type of insurance plan known to the system 130 in the form of, e.g., a Boolean yes/no estimate or a scalar value representing a probability. In other embodiments, the classification may indicate a confidence level that the insurance card matches a stored template of an insurance card, a probability that the insurance card is associated with a specific insurance company, or some combination thereof. The classification of the insurance card is stored in association with the user of the insurance card.

Once the insurance plan of the user is identified, the system 130 may analyze 630 the historical medical information of the user. The historical medical information may include prescription history, medical procedure history, medical claims, co-payment history, or any other relevant medical history of the user. The system 130 analyzes 630 the historical medical information of the user in the context of the identified insurance plan of the user. This analysis allows the system 130 to determine if the identified insurance plan is the most suitable insurance plan for the user. The insurance management system 130 may recommend 635 one or more alternative insurance plans to the user that are more suitable for the user based on the user's medical needs.

Figure 7:
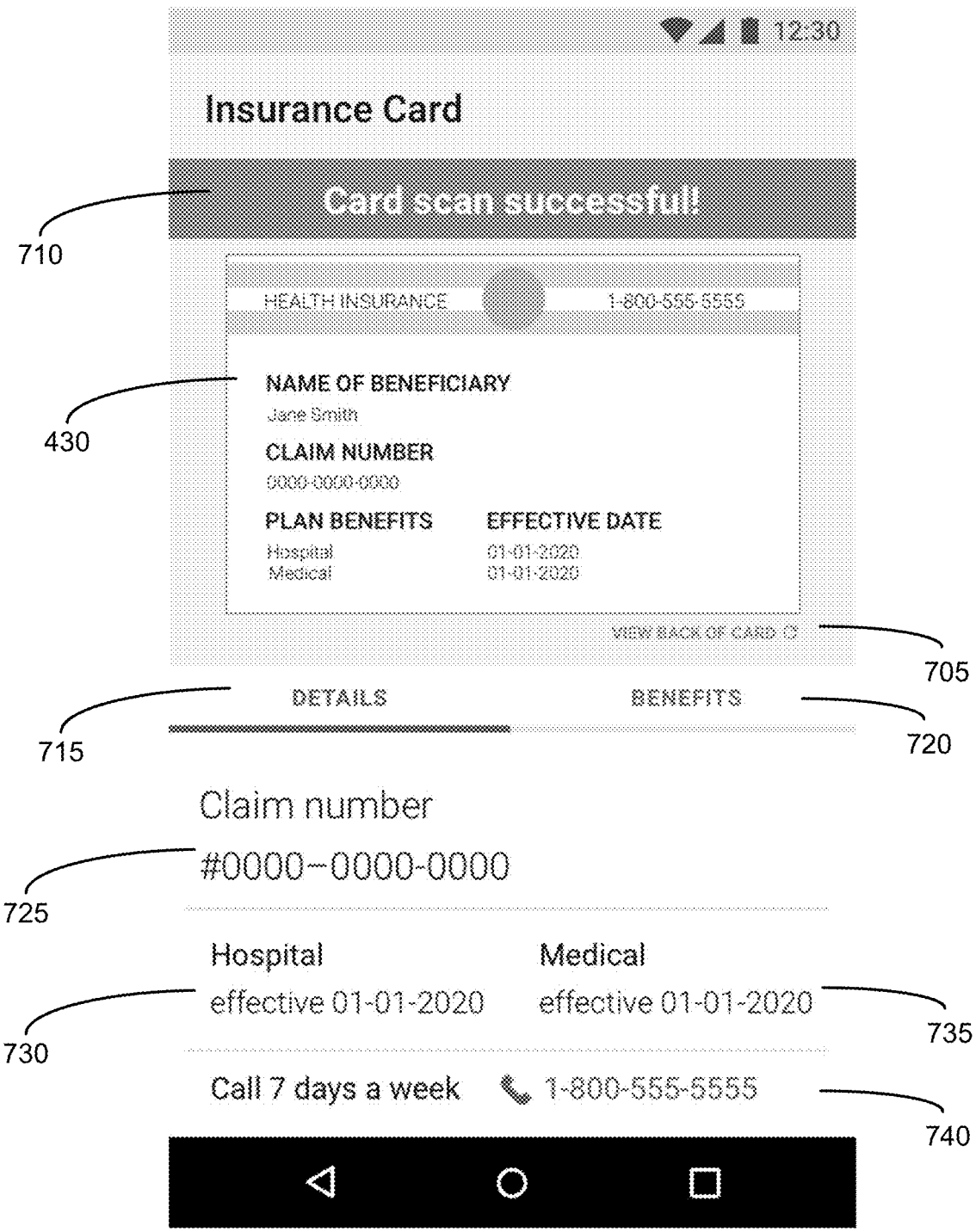
FIG. 7 illustrates a user interface for presenting information extracted from a captured image of an insurance card, in accordance with an embodiment.

FIG. 7 illustrates a user interface 700 for presenting information extracted from the captured image 430 of the insurance card 425, in accordance with an embodiment. The user interface 700 may be a user interface of an application executed on a client device 120 that allows a user to interact with the system 130 and access insurance information. In the embodiment of FIG. 7, the user interface 700 presents the captured image 430, which includes the front side of the insurance card 425. The user interface includes an option 705 that, when selected, allows the user to view a captured image of the back side of the insurance card 425. A notification 710 states "Card scan successful!," indicating that the insurance card 425 in the captured image 430 has been successfully scanned. A successful scan indicates that the captured image(s) of the insurance card 425 is of sufficient quality and that the system 130 is able to extract the information on the insurance card 425 from the captured image 430. The extracted information includes text, objects, and/or logos on the insurance card 425.

Once the information is extracted from the captured image 430, the system 130 presents the extracted information to the user in the user interface 700. As shown in FIG. 7, the user interface 700 includes a "Details" tab 715 and a "Benefits" tab 720. The "Details" tab 715 displays the extracted information by populating respective data fields in the user interface 700. For example, the extracted claim number populates data field 715, the extracted coverage effective dates populate data fields 720 and 725, and the extracted customer service number populates data field 730. The "Benefits" tab 720 may display the benefits information associated with the insurance plan identified in the insurance card 425. Benefits information may include co-payment information for in-network and out-of-network providers and/or procedures, deductible amount, out-of-pocket expense limits, or any other information relevant to an insurance plan. The system 130 may determine the benefits of the insurance plan using an internal database or a third party database or system. The data fields in the user interface 700 may be editable and selectable options so that, if the user identifies an error in the extracted information, the user can edit the extracted text and/or association of the text to a data field. Thus, if the user sees that a portion of a phone number has been associated as a date, the user can select the date and an option associating the date as part of the phone number via options presented to the user responsive to the user selecting the date.

Features Available to a User of the Insurance Management System

A user of the insurance management system 130 has access to various features associated with stored insurance information. The features may be accessed through a client device 120 of the user, and many of the features be automatically set up by the system 130 without requiring additional user input (or requiring minimal user input or simply user confirmation of a feature) after images of the insurance card of the user are captured. Example features include network updates, insurance benefits updates, payment history and management options, and insurance customer service access. A network update may be a feature specific to providers or procedures available in a user's network. An insurance benefit update may be a feature specific to benefits of the user's insurance plan. Payment history and management options include other features that may allow a user to track their medical claims, explanation of benefits (EOBs), health spending account (HSA) activity and/or balance, etc. Insurance customer service access may offer a method for conveniently contacting customer service at the insurance company. Additionally, in some embodiments, the system 130 may be integrated with a prescription management system or may have access to personal accounts of the user that provide historical medical information of the user to the system 130. In these embodiments, the system 130 may analyze the user's medical needs to determine if the insurance plan identified on the insurance card is the most suitable insurance plan for the user. The system 130 may recommend one or more alternative insurance plans that are more suitable for the user based on the user's medical needs or that may result in cost-savings for the user. The various features will be described in conjunction with FIGS. 7 and 8.

Figure 8:
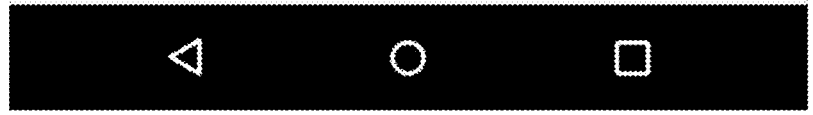
FIG. 8 is an example of an application feature for comparing insurance plans, in accordance with an embodiment.

FIG. 8 is an example of an application feature 800 for comparing insurance plans, in accordance with an embodiment. As illustrated in FIG. 8, the application feature 800 presents a financial overview 805 of the user's current insurance plan. The financial overview 805 includes the current annual cost of $647, the monthly premium of $28.90, the health deductible amount of $0, and the drug deductible amount of $300. Additional information may be presented to the user that highlights the costs associated with the user's insurance plan (e.g., average out-of-pocket expense, percentage of deductible used, etc.).

The application feature 800 additionally presents a first insurance plan, Plan Name A, and a second insurance plan, Plan Name B. The system 130 may select the first insurance plan and the second insurance plan from a database of stored insurance plans. The insurance plans may be selected based on an analysis of the user's historical medical information (e.g., prescription history, medical claims history, etc.), the benefits offered by each insurance plan, and the estimated cost savings compared to the user's current insurance plan. The system 130 may perform the analysis without requiring user input into the user interface of the application and may provide a notification to the user through the user interface that informs the user that a recommendation for alternative insurance plans is available. For example, the system 130 may detect that a user has several recurring prescriptions based on payment history of the user. If the user's current insurance plan does not cover or only partially covers the cost for the prescriptions, or has a high drug deductible, the user may have high out-of-pocket expenses. An insurance plan that has a lower drug deductible or that covers a larger portion of the costs of the prescriptions may be a better suited insurance plan for the user based on the user's medical needs. As illustrated in FIG. 8, the application feature 800 presents a financial overview 810, 815 for each selected plan, Plan Name A and Plan Name B, respectively, that shows the estimated annual costs of the plan and compares the annual savings of the plan compared to the user's current insurance plan. The financial overviews 810, 815 may include a link to view the full benefits of the plan. The application feature 800 may be further configured to connect the user with a representative at the insurance company of the alternative plan and/or schedule a phone call for the user during open enrollment dates. While FIG. 8 presents two alternative insurance plans, the number of alternative insurance plans presented may vary in other embodiments.

FIG. 9 is an example of an application feature 900 for comparing medication co-payments, in accordance with an embodiment. As illustrated in FIG. 9, the application feature 900 presents a financial overview 905 that compares a user's prescription co-payment costs at the user's current pharmacy and possible annual savings for the user if the user switches to a second pharmacy. The application feature 900 presents a financial breakdown 910 of the user's prescription costs at the user's current pharmacy and a financial breakdown 915 of the user's prescription costs at an alternative pharmacy. The financial breakdowns 910, 915 list each prescription of the user and the respective insurance plan contribution and individual contribution for each prescription. The system 130 may select the alternative pharmacy based on an analysis of the user's prescription payment history, insurance plan benefits, pharmacies in the network of the user's insurance plan, pharmacy proximity to the user, and any other relevant factor, or some combination thereof. The application feature 900 may offer an option 920 that allows a user to change their current pharmacy.

In some embodiments, the application associated with the insurance management system 130 that is executed on the client device 120 may have additional features that allow a user to manage their insurance and/or medical information. For example, the application may allow the user to import medical claims, EOBs, and insurance payments. The user interface on the application may display this information to the user in an easily navigable manner. The application may be further configured to highlight duplicates, errors, and/or outstanding payments, reimbursements, or claims.

In some embodiments, the application may have additional features that allow a user to manage their insurance and/or medical information for future planning. For example, the system 130 may analyze patterns of the user based on procedure history, claims history, payment history, etc. The system 130 may run a user-specific simulation that can inform the user of their predicted health spending account usage, deductible tracking, etc. and make recommendations to the user based on the simulation. For example, the system 130 may be aware that the user has been wanting to receive corrective eye surgery. Based on analysis of the user's patterns, the system may recommend an appropriate timing for the user to receive the corrective eye surgery (e.g., "You're on track to meet your deductible by June; this might be a good time to schedule the corrective eye surgery.").

Any one or more of the features described above can be automatically set up for the user based merely on the user having taken an image to capture insurance plan information. Thus, the user does not have to manually input information as this information can be automatically done by the system. In one embodiment, the system 130 automatically sets up these features for the user based on the information extracted from the captured image of the insurance card such that the user automatically starts receiving recommendations or can access the recommendations after capturing the image. In another embodiment, the system 130 automatically provides a prompt to the user to confirm to have these features set up or otherwise collects information/input needed from the user for setting up these features. In a further embodiment, the user provides preferences upon initially setting up an account (e.g., I would like recommendations for cost-saving insurance plans), and these preferences are applied in automatically setting up these features as images are taken of an insurance card.

Additional Considerations

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method comprising:
training, by a processor, a set of images of insurance cards for a machine learning model, wherein inputs to the machine learning model comprise historical data for one or more classifications associated with one or more types of insurance cards during a historical time period, wherein outputs of the machine learning model comprise at least one insurance plan matching at least one classification of the one or more classifications associated with the one or more types of insurance cards, wherein each classification of the one or more classifications is associated with a respective insurance plan;
receiving, by the processor, at least one image of an insurance card of a user scanned from a mobile device of the user;
extracting, by the processor, one or more feature values from the at least one image of the insurance card of the user, the one or more feature values, as extracted, comprising of text information, object information, color information, and shape information;
generating, by the processor, a feature vector associated with the at least one image of the insurance card of the user comprising an ordered list of the one or more feature values, as extracted, for the at least one image of the insurance card of the user;

reducing an amount of data in the feature vector of the at least one image of the insurance card of the user to a set of data using dimensionality reduction;

determining, by the machine learning model, as trained, a first insurance plan of the user based on input data comprising the set of data of the feature vector, as reduced, of the at least one image of the insurance card of the user;

storing, by the processor, the first insurance plan, as determined;

receiving, by the processor, historical medical information of the user comprising medical conditions of the user;

identifying, by the processor, at least one alternative insurance plan to be displayed to the user, comprising:
   evaluating, based in part on the historical medical information associated with the user, the first insurance plan, as determined, of the user;
   generating a comparison of a plurality of feature values of the first insurance plan of the user to other feature values of one or more alternative insurance plans, wherein the other feature values comprise one or more of the following:
      (i) one or more respective benefits associated with the first insurance plan of the user and each alternative insurance plan of the one or more alternative insurance plans;
      (ii) a respective cost associated with the first insurance plan of the user and the each alternative insurance plan; and
      (iii) a respective savings associated with the each alternative insurance plan relative to the first insurance plan of the user; and
   selecting the at least one alternative insurance plan of the one or more alternative insurance plans based on the comparison; and sending, by the processor, instructions to display to the user on a user interface of the mobile device of the user a recommendation comprising the at least one alternative insurance plan, as selected.

2. The method of claim 1, wherein the text information includes one or more of the following:
   a patient name, an insurance carrier name, an insurance plan name, a patient identification number, an issuer identification number, a group number, a coverage effective date, an employer name, a bank identification number (BIN), co-payment information, or a customer service number.

3. The method of claim 1, wherein the historical medical information comprises one or more of the following:
   a prescription history, a medical expense history, a medical claims history, a medical procedure history, or a co-payment history of the user.

4. The method of claim 1, further comprising:
   forming a positive training set of images of other insurance cards that are classified as associated with the respective insurance plan or a respective insurance company;
   providing the positive training set to the machine learning model for training of the machine learning model;
   forming a negative training set of images of the other insurance cards that are classified as not associated with the respective insurance plan or the respective insurance company; and
   providing the negative training set to the machine learning model for training of the machine learning model.

5. The method of claim 1, wherein the user interface of the mobile device of the user displays the comparison between the first insurance plan of the user and the one or more alternative insurance plans for the user.

6. The method of claim 1, wherein:
   the historical medical information of the user further comprises:
      a pharmacy of the user; and
   the recommendation further comprises:
      one or more alternative pharmacies for the user to consider as alternatives to the pharmacy of the user.

7. The method of claim 6, further comprising:
   selecting the one or more alternative pharmacies for the recommendation based on an analysis of one or more of the following:
      (i) respective prescription co-payment costs associated with each pharmacy, (ii) a respective savings associated with each of the one or more alternative pharmacies relative to the pharmacy of the user, (iii) a respective proximity of the each pharmacy to the user, (iv) a respective network associated with the each pharmacy, or (v) respective insurance plan benefits associated with the each pharmacy.

8. The method of claim 6, wherein the user interface of the mobile device of the user displays a comparison between the pharmacy of the user and the one or more alternative pharmacies for the user, the comparison comprising one or more of the following:
   (i) respective prescription co-payment costs associated with each pharmacy, (ii) a respective savings associated with each of the one or more alternative pharmacies relative to the pharmacy of the user, (iii) a respective proximity of the each pharmacy to the user, (iv) a respective network associated with the each pharmacy, or (v) respective insurance plan benefits associated with the each pharmacy.

9. The method of claim 1, further comprising:
   analyzing a medical expense history of the user, the medical spending history comprising one or more of health spending account contributions, health spending account usage, deductible tracking, and out-of-pocket expenses of the user;
   determining a financial prediction for the user based on the medical expense history; and
   providing the recommendation based on the financial prediction, wherein the recommendation comprises a recommended timeframe for medical visits or medical procedures for the user.

10. The method of claim 1, wherein the machine learning model is configured to:
   determine, based on a set of feature values, a template of a first insurance card that is similar to the insurance card of the user in the at least one image, wherein the template is a geometrical representation of the first insurance card known to an insurance management system and comprises one or more slots in various locations on the template where each slot is associated with a respective type of information.

11. A non-transitory computer-readable storage media storing computing instructions that, when executed by one or more processors, cause the one or more processors to perform:
   training, by a processor, a set of images of insurance cards for a machine learning model, wherein inputs to the machine learning model comprise historical data for one or more classifications associated with one or more types of insurance cards during a historical time period, wherein outputs of the machine learning model comprise at least one insurance plan matching at least one classification of the one or more classifications associated with the one or more types of insurance cards, wherein each classification of the one or more classifications is associated with a respective insurance plan;

receiving, by the processor, at least one image of an insurance card of a user scanned from a mobile device of the user;

extracting, by the processor, one or more feature values from the at least one image of the insurance card of the user, the one or more feature values, as extracted, comprising text information, object information, color information, and shape information;

generating, by the processor, a feature vector associated with the at least one image of the insurance card of the user comprising an ordered list of the one or more feature values, as extracted, for the at least one image of the insurance card of the user;

reducing an amount of data in the feature vector of the at least one image of the insurance card of the user to a set of data using dimensionality reduction;

determining, by the machine learning model, as trained, a first insurance plan of the user based on input data comprising the set of data of the feature vector, as reduced, of the at least one image of the insurance card of the user;

storing, by the processor, the first insurance plan, as determined;

receiving, by the processor, historical medical information of the user comprising medical conditions of the user;

identifying, by the processor, at least one alternative insurance plan to be displayed to the user, comprising:
evaluating, based in part on the historical medical information associated with the user, the first insurance plan, as determined, of the user;
generating a comparison of a plurality of feature values of the first insurance plan of the user to other feature values of one or more alternative insurance plans, wherein the other feature values comprise one or more of the following:
(i) one or more respective benefits associated with the first insurance plan of the user and each alternative insurance plan of the one or more alternative insurance plans;
(ii) a respective cost associated with the first insurance plan of the user and the each alternative insurance plan; and
(iii) a respective savings associated with the each alternative insurance plan relative to the first insurance plan of the user; and
selecting the at least one alternative insurance plan of the one or more alternative insurance plans based on the comparison; and sending, by the processor, instructions to display to the user on a user interface of the mobile device of the user a recommendation comprising the at least one alternative insurance plan, as selected.

12. The non-transitory computer-readable storage medium of claim 11, wherein the computing instructions further causing the one or more processors to perform further comprises:

forming a positive training set of images of other insurance cards that are classified as associated with the respective insurance plan or a respective insurance company;
providing the positive training set to the machine learning model for training of the machine learning model;
forming a negative training set of images of the other insurance cards that are classified as not associated with the respective insurance plan or the respective insurance company; and
providing the negative training set to the machine learning model for training of the machine learning model.

13. The non-transitory computer-readable storage medium of claim 11, wherein the user interface of the mobile device of the user displays the comparison between the first insurance plan of the user and the one or more alternative insurance plans for the user.

14. The non-transitory computer-readable storage medium of claim 11, wherein:
the historical medical information of the user further comprises:
a pharmacy of the user; and
the recommendation further comprises:
one or more alternative pharmacies for the user to consider as alternatives to the pharmacy of the user.

15. The non-transitory computer-readable storage medium of claim 14, wherein the computing instructions further causing the one or more processors to perform further comprises:
selecting the one or more alternative pharmacies for the recommendation based on an analysis of one or more of the following:
(i) respective prescription co-payment costs associated with each pharmacy, (ii) a respective savings associated with each of the one or more alternative pharmacies relative to the pharmacy of the user, (iii) a respective proximity of the each pharmacy to the user, (iv) a respective network associated with the each pharmacy, or (v) respective insurance plan benefits associated with the each pharmacy.

16. The non-transitory computer-readable storage medium of claim 14, wherein the user interface of the mobile device of the user displays a comparison between the pharmacy of the user and the one or more alternative pharmacies for the user, the comparison comprising one or more of the following:
(i) respective prescription co-payment costs associated with each pharmacy, (ii) a respective savings associated with each of the one or more alternative pharmacies relative to the pharmacy of the user, (iii) a respective proximity of the each pharmacy to the user, (iv) a respective network associated with the each pharmacy, or (v) respective insurance plan benefits associated with the each pharmacy.

17. The non-transitory computer-readable storage medium of claim 11, wherein the computing instructions further causing the one or more processors to perform further comprises:
analyzing a medical expense history of the user, the medical spending history comprising one or more of health spending account contributions, health spending account usage, deductible tracking, and out-of-pocket expenses of the user;
determining a financial prediction for the user based on the medical expense history; and providing the recommendation based on the financial prediction, wherein the recommendation comprises a recommended timeframe for medical visits or medical procedures for the user.

18. The non-transitory computer-readable storage medium of claim 11, wherein the machine learning model is configured to:
determine, based on a set of feature values, a template of a first insurance card that is similar to the insurance card of the user in the at least one image, wherein the template is a geometrical representation of the first insurance card known to an insurance management system and comprises one or more slots in various locations on the template where each slot is associated with a respective type of information.

19. A system comprising:
one or more processors; and
one or more non-transitory computer-readable media storing computing instructions configured to run on the one or more processors and perform:
training, by a processor, a set of images of insurance cards for a machine learning model, wherein inputs to the machine learning model comprise historical data for one or more classifications associated with one or more types of insurance cards during a historical time period, wherein outputs of the machine learning model comprise at least one insurance plan matching at least one classification of the one or more classifications associated with the one or more types of insurance cards, wherein each classification of the one or more classifications is associated with a respective insurance plan;
receiving, by the processor, at least one image of an insurance card of a user scanned from a mobile device of the user;
extracting, by the processor, one or more feature values from the at least one image of the insurance card of the user, the one or more feature values, as extracted, comprising text information, object information, color information, and shape information;
generating, by the processor, a feature vector associated with the at least one image of the insurance card of the user comprising an ordered list of the one or more feature values, as extracted, for the at least one image of the insurance card of the user;
reducing an amount of data in the feature vector of the at least one image of the insurance card of the user to a set of data using dimensionality reduction;
determining, by the machine learning model, as trained, a first insurance plan of the user based on input data comprising the set of data of the feature vector, as reduced, of the at least one image of the insurance card of the user;
storing, by the processor, the first insurance plan, as determined;
receiving, by the processor, historical medical information of the user comprising medical conditions of the user;
identifying, by the processor, at least one alternative insurance plan to be displayed to the user, comprising:
evaluating, based in part on the historical medical information associated with the user, the first insurance plan, as determined, of the user;
generating a comparison of a plurality of feature values of the first insurance plan of the user to other feature values features of one or more alternative insurance plans, wherein the other feature values comprise one or more of the following:
(i) one or more respective benefits associated with the first insurance plan of the user and each alternative insurance plan of the one or more alternative insurance plans;
(ii) a respective cost associated with the first insurance plan of the user and the each alternative insurance plan; and
(iii) a respective savings associated with the each alternative insurance plan relative to the first insurance plan of the user; and
selecting the at least one alternative insurance plan of the one or more alternative insurance plans based on the comparison; and
sending, by the processor, instructions to display to the user on a user interface of the mobile device of the user a recommendation comprising the at least one alternative insurance plan, as selected.

20. The system of claim 19, wherein the computing instructions are further configured to run on the one or more processor and perform further comprises:
determining, by the processor, based on a set of feature values, a template of a first insurance card that is similar to the insurance card of the user in the at least one image, wherein the template is a geometrical representation of the first insurance card known to an insurance management system and comprises one or more slots in various locations on the template where each slot is associated with a respective type of information.

21. The system of claim 20, wherein the classification further comprises a confidence level that the insurance card of the user in the at least one image matches the template.

22. The system of claim 19, wherein training the machine learning model comprises:
calculating a difference between a determined classification and a received classification of a particular insurance card, wherein the received classification comprises an identification of the insurance plan associated with the particular insurance card; and
adjusting, based on the difference, one or more coefficients of the machine learning model to reduce the difference.

23. The system of claim 19, wherein the computing instructions are further configured to run on the one or more processor and perform further comprises:
forming a positive training set of images of other insurance cards that are classified as associated with the respective insurance plan or a respective insurance company; and
providing the positive training set to the machine learning model for training of the machine learning model.

24. The system of claim 19, wherein the computing instructions are further configured to run on the one or more processor and perform further comprises:
forming a negative training set of images of the other insurance cards that are classified as not associated with the respective insurance plan or a respective insurance company; and
providing the negative training set to the machine learning model for training of the machine learning model.

25. The system of claim 19, wherein the computing instructions are further configured to run on the one or more processor and perform further comprises:
forming a validation training set of images of the other insurance cards that are classified as associated or not associated with a respective insurance plan or a respective insurance company; and providing the validation training set of images of the other insurance cards to the machine learning model for training of the machine learning model.

26. The system of claim 19, wherein:

the historical medical information of the user further comprises:

a pharmacy of the user; and the recommendation further comprises:

one or more alternative pharmacies for the user to consider as alternatives to the pharmacy of the user.

27. The method of claim 1, wherein extracting the one or more feature values from the at least one image of the insurance card of the user further comprises:

(i) using one or more text recognition algorithms, (ii) one or more object recognition algorithms, (iii) one or more feature recognition algorithms, or (iv) some combination thereof.

28. The method of claim 10, further comprising:

populating, by the processor, each of a plurality of particular data fields in the template with one or more respective feature values, as extracted, that represent a respective correct type of feature to fill the each of the plurality of particular data fields.

\* \* \* \* \*